US00PP13039P2

(12) United States Plant Patent
Bessho

(10) Patent No.: US PP13,039 P2
(45) Date of Patent: Oct. 1, 2002

(54) CALIBRACHOA PLANT NAMED 'KAKEGAWA S24'

(75) Inventor: Masao Bessho, Kakegawa (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 09/709,937

(22) Filed: Nov. 13, 2000

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Rothwell, Figg, Ernst & Manbeck

(57) ABSTRACT

Disclosed herein is a new and distinct Calibrachoa plant, and its parts, named 'Kakegawa S24' having a creeping plant habit, abundant branching and pure white petal colors.

1 Drawing Sheet

BACKGROUND OF THE NEW PLANT

This invention relates to a new and distinct cultivar of Calibrachoa plant, hereinafter referred to by the name 'Kakegawa S24'. 'Kakegawa S24' is a new variety of Calibrachoa plant having a creeping, branching habit. The plant grows vigorously and makes an excellent hanging basket. The invention's flowers are funnel shaped with five-fissured limbs, and a slight indent on each petal. The flowers are single with a diameter of 3.0–3.7 cm when fully open. The petals are pure white with a pale yellow-green corolla throat (RHS 154C). The plant grows and flowers best under low soil pH conditions (pH 5–6). Typically young flowers will close under low light and low temperature conditions such as late in the day or at night.

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of *P. hybrida,* the Garden Petunia, and the inter-relationship of several species classified as Petunia. These studies revealed that *P. hybrida* and its ancestral species, *P. nyctaginiflora* (=*P. axillaris*) and *P. violacea* (=*P. integrifolia*), possessed 14 pairs of chromosomes while several other species, including *P. parviflora,* possessed 18 pairs of chromosomes. Since *P. parviflora* was the lectotype species for the Petunia genus, Wijsman and J. H. deJong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome species to another genus. The I.N.G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana la Lave & Lexarza*) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud estivation. Whereas, Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

Asexual reproduction of 'Kakegawa S24' Calibrachoa originated from a hybridization made in 1996 by the Sakata Seed Corporation, Kakegawa breeding station in Kakegawa, Japan. The female parent was a deep rose (red-pink) petaled, decumbent habit plant known as 'Liricashower Rose', a plant described and illustrated in U.S. Plant Pat. No. 9,884. The male parent was a white flowered, decumbent habit breeding line known only as 'White #1'. The initial cross-pollination of the parents resulting in $F_1$ generation seed, was made in October, 1996. In February, 1997, the $F_1$ seed was sown and yielded 15 plants. From these 15 plants, three plants were selected for appealing flower color and creeping, branching plant habit. That summer the three selected plant lines were intercrossed to produce $F_2$ seed.

In February, 1998 the second generation seed was planted in the field at Kakegawa, Japan. Five plants were selected from the $F_2$ generation for their white flower color and creeping, branching plant habit. These five plants were asexually reproduced and tested for easy reproducibility and stability of traits. In 1999 three of these lines were selected and propagated again for evaluation. Trait stability was confirmed in all three lines in greenhouses in Japan.

Also in 1999, cuttings of this plant line were sent California. During this Summer plants were grown under the direction and supervision of the inventor for evaluation of stability of the line's desired traits. Plants were evaluated in hanging pots at the research station in Salinas, Calif. Final selection of one line as the new variety was made in California. The present invention, 'Kakegawa S24' Calibrachoa was determined by the inventor to have it's characteristics, as herein described, firmly fixed.

The plant was asexually produced by excising the terminal 1.0 to 1.5 inches of an actively growing stem. The basal half is stripped of leaves and dipped in a 1:19 dilution of Dip-N-Gro™ rooting solution (solution: water). Plastic cell trays with a 1.0 inch diameter by 1.5 inch deep cells are filled with a peat-moss based growing media. The basal portion of the stem is then inserted into moistened peat-moss media. The cuttings are kept in a warm greenhouse under a clear plastic tent with occasional misting from an automatic watering system. The cuttings are fully rooted in six weeks.

BRIEF DESCRIPTION OF THE DRAWINGS

The accompanying drawings serve by color photographic means to illustrate the new plant variety, 'Kakegawa S24'. The colors are represented as true as possible using conventional photographic procedures.

DETAILED DESCRIPTION OF THE NEW VARIETY

Figure 1:
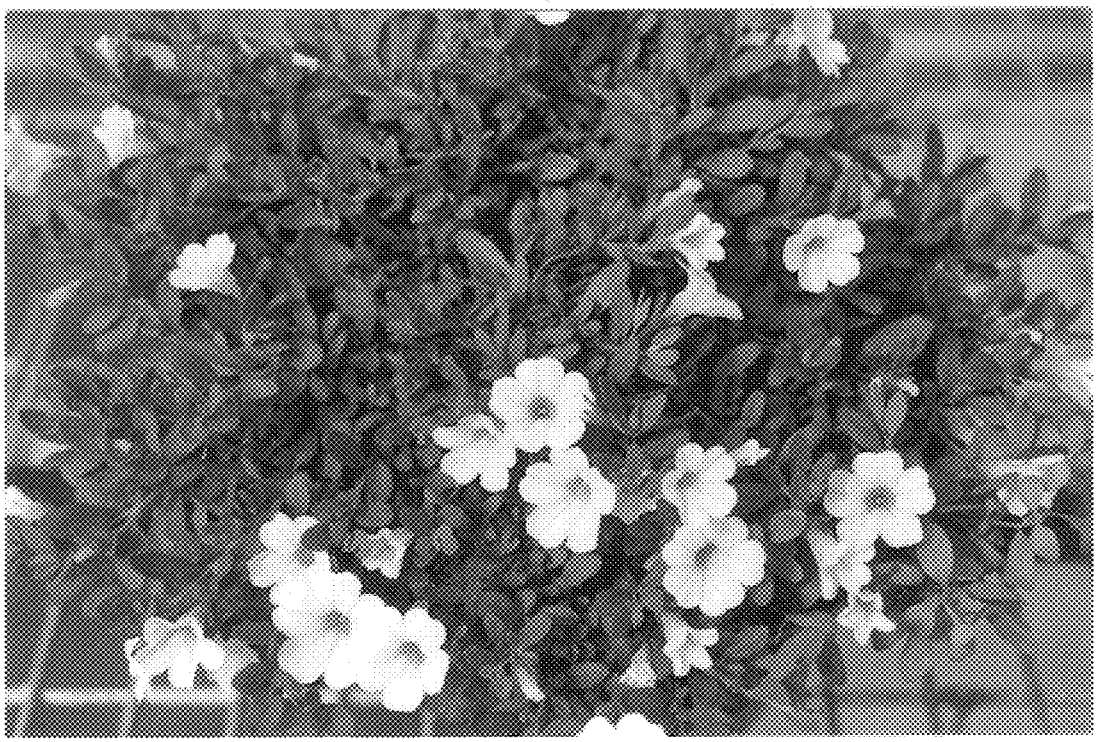
FIG. 1 is a close-up view of multiple blooms illustrating the creeping habit; abundant branching; and flower morphology.
Figure 2:
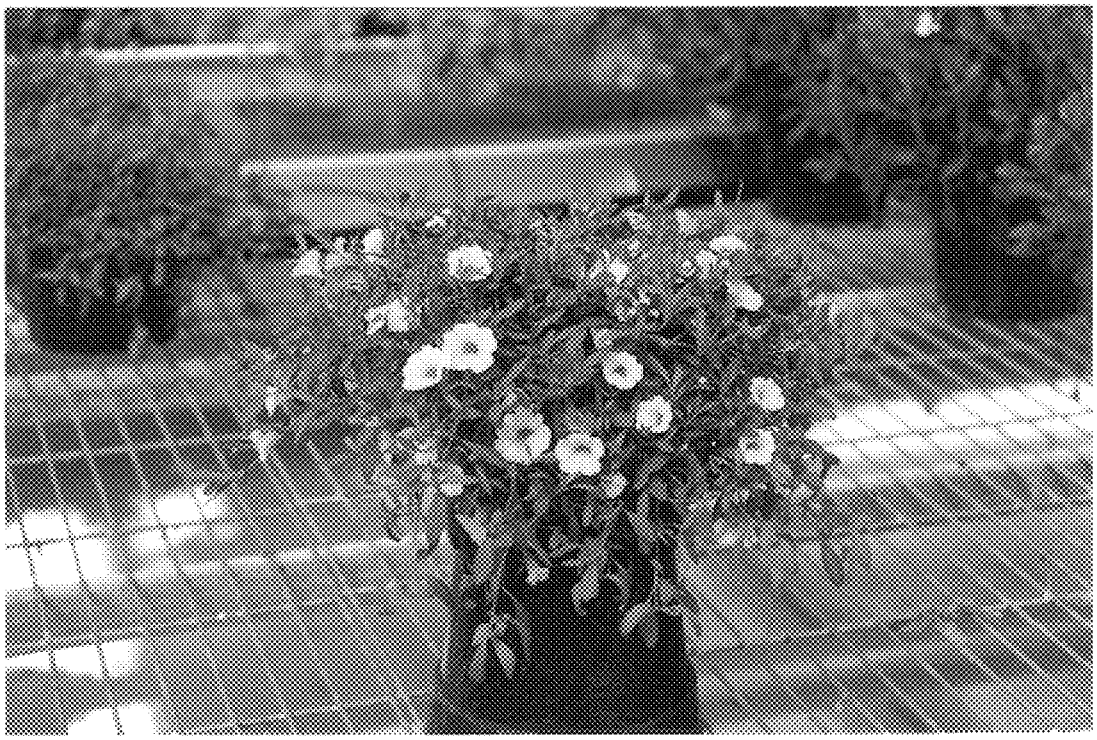
FIG. 2 is a view of the new cultivar after growing for several weeks in a six-inch greenhouse pot.

The following description is based on observations and measurements of pot grown plants in Salinas, Calif. Data was collected on plants six weeks after individually transplanting rooted cuttings to a six inch pot. Color designations were made according to The Royal Horticultural Society Colour Chart (R.H.S.) published by The Royal Horticultural Society of London, England.

Origin: Seedling.

Parentage: This new variety is a selection from the $F_2$ progeny of three intercrossed $F_1$ plants derived from the cross of 'Liricashower Rose' (U.S. Plant Pat. No. 9,884) with Breeding Line 'White #1' (an unpatented plant).

Classification:

*Family*.—Solanaceae.
*Genus*.—Calibrachoa.
*Botanical*.—Calibrachoa sp.
*Commercial*.—'Kakegawa S24'.

Plant:

*Growth habit*.—Creeping; strongly branching.
*Plant height*.—Varies depending on the container size; a hanging basket measuring 40 cm in diameter will produce a plant 40 to 50 cm in length and 70 to 90 cm in width.
*Time to produce a rooted cutting*.—Six weeks for full root development in a plastic cell tray with 1.0 inch diameter by 1.5 inch deep cells.
*Life cycle*.—Perennial.

Stem:

*Thickness*.—1.0 mm.
*Color*.—Light green (144B).
*Pubescence*.—Slight.
*Branching*.—Abundant.
*Internode length*.—1.0–3.0 cm.

Leaf:

*Apex*.—Mucronate.
*Base*.—Oblique.
*Arrangement*.—Verticillate.
*Color*.—Upper leaf color is green RHS 137A; lower leaf color is green RHS 137B.
*Pubescence*.—Moderate on upper and lower surfaces; pubescence is short, colorless and bulbous at the tip.
*Fragrance*.—None.
*Shape*.—Elliptic.
*Length* (*average*).—3.2 cm at full expansion.
*Margin*.—Entire.
*Surface*.—Slightly pubescent; dull.
*Variegation*.—None.
*Venation*.—Pinnate.
*Width* (*average*).—0.9 cm at full expansion.

Flower:

*Blooming period*.—Plants bloom with long days starting in March and continuing into October. Each bloom lasts three days. Blooms stay open all day and night. Blooms are fairly cold tolerant but will not withstand freezing temperatures.
*Quantity*.—Mature plants growing in a six inch diameter pot can have in excess of 100 open flowers. The inflorescence is solitary.
*Calyx*.—5 sepals; 1.5 cm length×0.4 cm width.
*Corolla*.—5 petals; fused.
*Diameter*.—3.0–3.7 cm.
*Shape*.—The flowers are funnel shaped with five fissures and a shallow, yet prominent, indentation of the petal tip at the midvein. Flower depth is approximately two-thirds of flower diameter or 1.0–1.3 cm. Petal fusion is invisible and has a length of 0.8–1.0 cm.
*Fragrance*.—None.
*Habit*.—Indeterminate.
*Inflorescence type*.—Solitary.
*Ovary*.—Superior.
*Pedicel length*.—1.0–1.4 cm.
*Stamen color*.—Yellow RHS 3B anthers.
*Stigma color*.—Green RHS 143D.
*Style color*.—Green RHS 143D.
*Placenta arrangement*.—Central.
*Petal pubescence*.—Glabrous.
*Petal color*.—Upper and lower surfaces are pure white with RHS 154C (pale yellow-green) midveins; corolla tube inner and outer surfaces are yellow-green RHS 154B; and corolla throat is pure white.
*Petal size*.—2.5–3.0 cm length×1.5–1.8 cm width.
*Pollen color*.—RHS 3C (yellow).
*Stamens*.—5.
*Fruit & seeds*.—No seeds or fruits are produced.

Disease/pests: Plants are susceptible to Botrytis, powdery mildew, various stem and root rots and certain viruses like Tobacco Mosaic Virus and Impatiens Necrotic Spotted Virus. Plants can be infested with aphids, leafminer, whitefly and various Lepitopdera. Plants are cold tolerant and can overwinter under snow cover.

Comparison With Other Known Varieties

The new variety is distinguished from other Calibrachoa plants by its pure white petal color and creeping habit. The closest commercial cultivar to this new variety that we are aware of is the petunia-like plant named 'Million Bells Trailing White'. The distinguishing characteristics which differentiate 'Kakegawa S24' from 'Million Bells Trailing White' are:

| | 'Kakegawa S24' | 'Million Bells Trailing White' |
|---|---|---|
| Plant Habit | Creeping | Mounding |
| Internode Length | 1.0–3.0 cm | 0.5–1.8 cm |
| Flower Color | Pure white with a pale yellow-green corolla tube and yellow-green mid veins | Pure white with a pale yellow corolla tube and yellow mid veins |
| Flower Size | 3.0–3.7 cm | 2.0–3.0 cm |

We claim:

1. A new and distinct cultivar of Calibrachoa plant herein referred to by the name 'Kakegawa S24', substantially as herein illustrated and described.

* * * * *